US007041296B1

(12) United States Patent
Stober et al.

(10) Patent No.: US 7,041,296 B1
(45) Date of Patent: May 9, 2006

(54) METHODS OF TREATING INFLAMMATORY BOWEL DISEASE USING CHOLERA TOXIN B SUBUNIT

(75) Inventors: Warren Stober, Bethesda, MD (US); Ivan J. Fuss, Bethesda, MD (US); Brian L. Kelsall, Washington, DC (US); Monica Boirivant, Rome (IT)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/129,907

(22) PCT Filed: Nov. 9, 2000

(86) PCT No.: PCT/US00/30837

§ 371 (c)(1),
(2), (4) Date: Sep. 17, 2002

(87) PCT Pub. No.: WO01/34175

PCT Pub. Date: May 17, 2001

Related U.S. Application Data

(60) Provisional application No. 60/165,111, filed on Nov. 12, 1999.

(51) Int. Cl.
*A61K 39/00* (2006.01)

(52) U.S. Cl. .............................. 424/184.1; 424/234.1; 424/203.1; 424/252.1; 424/145.1; 424/158.1; 530/300; 530/350; 514/2

(58) Field of Classification Search ............. 424/152.1, 424/130.1, 133.1, 141.1, 85.2, 145.1, 184.1, 424/240.1, 241.1, 194.1, 204.1, 236.1, 244.1, 424/282.1, 261.1, 275.1, 449, 450, 9.2, 158.1, 424/234.1, 203.1, 252.1; 514/12, 2, 8; 530/350, 530/300, 403
See application file for complete search history.

(56) References Cited

U.S. PATENT DOCUMENTS

| 4,411,888 | A | * | 10/1983 | Klipstein et al. | ......... | 424/194.1 |
| 5,214,029 | A | * | 5/1993 | Viallet et al. | .................. | 514/12 |
| 5,681,571 | A | * | 10/1997 | Holmgren et al. | ........ | 424/236.1 |
| 5,762,931 | A | * | 6/1998 | Talwar et al. | ............. | 424/138.1 |
| 5,882,653 | A | * | 3/1999 | Kaper et al. | .............. | 424/261.1 |
| 5,980,898 | A | * | 11/1999 | Glenn et al. | ............... | 424/184.1 |
| 6,019,973 | A | * | 2/2000 | Holmgren et al. | ........ | 424/185.1 |
| 6,030,624 | A | * | 2/2000 | Russell et al. | ........... | 424/200.1 |
| 6,153,203 | A | * | 11/2000 | Holmgren et al. | ........ | 424/236.1 |
| 6,255,097 | B1 | * | 7/2001 | Meyer et al. | ............. | 435/235.1 |
| 6,287,563 | B1 | * | 9/2001 | Williams et al. | ......... | 424/184.1 |
| 6,290,962 | B1 | * | 9/2001 | Michetti et al. | ......... | 424/185.1 |
| 6,322,796 | B1 | * | 11/2001 | Holmgren et al. | ....... | 424/236.1 |
| 6,365,163 | B1 | * | 4/2002 | Holmgren et al. | ....... | 424/236.1 |
| 6,376,460 | B1 | * | 4/2002 | Llewellyn-Smith | ............ | 514/2 |
| 6,440,413 | B1 | * | 8/2002 | Hooreman | ............... | 424/94.63 |
| 6,576,244 | B1 | * | 6/2003 | Weltzin et al. | ........... | 424/234.1 |
| 6,599,509 | B1 | * | 7/2003 | Fox et al. | ................ | 424/234.1 |
| 6,607,732 | B1 | * | 8/2003 | Morein et al. | ........... | 424/278.1 |
| 6,749,856 | B1 | * | 6/2004 | Berzofsky et al. | ....... | 424/188.1 |
| 2002/0044938 | A1 | * | 4/2002 | Fox et al. | ................ | 424/184.1 |
| 2003/0049797 | A1 | * | 3/2003 | Yuki et al. | ................. | 435/69.7 |

FOREIGN PATENT DOCUMENTS

| WO | WO 97/02045 | | 1/1997 |
| WO | 97/05267 | * | 2/1997 |
| WO | WO 98/16248 | | 4/1998 |
| WO | 99/18225 | * | 4/1999 |
| WO | WO 99/54452 | | 10/1999 |

OTHER PUBLICATIONS

Dr. Varga Laszlo et al, Allergy to Helicobacter pylori, Kazuisztika, pp. 359-361, Issue 6, 1992, English translation.*
Whary, MT et al, Infection and Immunity, vol. 66(7), apges 3142-3148, Jul. 1998, Chronic Active Hepatitis induced by Helicobacter hepaticus in the A/JCr Mouse is associated with a Th1 cell mediated immune response.*
Boirivant, M et al, The Journal of Immunology, 2001, vol. 166, pp. 3522-3532.*
Johnansson, E et al, Infection and Immunity, Feb. 1998, pp. 514-520, vol. 66(2).*
Kim, P et al, The Journal of Immunology, 1998, vol. 160, p. 1198-1203.*
Rudin, A et al, Infection and Immunity, Jul. 1998, pp. 3390-3396, vol. 66(7).*
Sobel, DO et al, Diabetes, vol. 47, pp. 186-191, 1998.*
Boirivant, M et al, The Journal of Immunology, 2001, Vol. 166, pp. 3522-3532.*
Johnansson, E et al, Infection and Immunity, Feb. 1998, pp. 514-520, Vol. 66(2).*
Kim, P et al, The Journal of Immunology, 2001, Vol. 166, pp. 1198-1203.*
Rudin, A et al, Infection and Immunity, Jul. 1998, pp. 3390-3396, Vol. 66(7).*

(Continued)

*Primary Examiner*—Lynette R. F. Smith
*Assistant Examiner*—Ginny Allen Portner
(74) *Attorney, Agent, or Firm*—Needle & Rosenberg, P.C.

(57) ABSTRACT

The present invention provides a method of treating or preventing inflammation in a subject, comprising administering to the subject an effective amount of cholera toxin subunit B. The present invention also provides a method of decreasing the activity of interferon gamma in a subject, comprising administering to the subject an effective amount of cholera toxin subunit B. Further provided is a method of decreasing the activity of IL-12 in a subject, comprising administering to the subject an effective amount of cholera toxin subunit B. Additionally, the present invention provides a method of treating or preventing a Th1 T-cell mediated autoimmune disorder in a subject, comprising administering to the subject an effective amount of cholera toxin subunit B.

21 Claims, No Drawings

OTHER PUBLICATIONS

Sobel, Do et al, *Diabetes*, Vol. 47, pp. 186-191, 1998.*

Bergerot et al., "A cholera toxoid-insulin conjugate as an oral vaccine against spontaneous autoimmune diabetes" *Proc. Natl. Acad. Sci. USA* 94:4610-4614 (Apr. 1997).

Boirivant et al., "Oral Administration of Recombinant Cholera Toxin Subunit B Inhibits IL-12 Mediated Murine Experimental Colitis" *Gastroenterology* 118 (4 pt. 1 Supp. 2):2982.

Boirivant et al., "Oral Administration of Recombinant Cholera Toxin Subunit B Inhibits IL-12-Mediated Murine Experimental (Trinitrobenzene Sulfonic Acid) Colitis" *J. Immunol.* 166(5):3522-3532 (Mar. 1, 2001).

Boirivant et al., "Oxazolone Colitis: A Murine Model of T Helper Cell Type 2 Colitis Treatable with Antibodies to Interleukin 4" *J. Exp. Med.* 188(10):1929-1939 (Nov. 16, 1998).

Braun et al., "Cholera Toxin Suppresses Interleukin (IL)-12 Production and IL-12 Receptor $\beta 1$ and $\beta 2$ Chain Expression" *J. Exp. Med.* 189(3):541-552 (Feb. 1, 1999).

Burkart et al., "Suppression of Autoimmune Diabetes by Cholera Toxin B Chain: Role of Innate Immunity" *Diabetologia* 42(Suppl. 1):A103.

de Haan et al., "Mutational analysis of role of ADP-ribosylation activity and $G_{m1}$-binding activity in the adjuvant properties of the *Escherichia coli* heat-labile enterotoxin towards intranasally administered keyhole limpet hemocyanin" *Eur. J. Immunol.* 28:1243-1250 (1998).

Douce et al., "Intranasal Immunogenicity and Adjuvanticity of Site-Directed Mutant Derivatives of Cholera Toxin" *Infection and Immunity* 65(7):2821-2828 (Jul. 1997).

Douce et al., "Mutants of *Escherichia coli* heat-labile toxin lacking ADP-ribosyltransferase activity act as nontoxic, mucosal adjuvants" *Proc. Natl. Acad. Sci. USA* 92:1644-1648 (Feb. 1995).

Elson et al., "Morphologic and Functional Alterations of Mucosal T Cells by Cholera Toxin and its B Subunit" *J. Immunol.* 154:1032-1040 (1995).

Elson, "Cholera Toxin as a Mucosal Adjuvant" *Mucosal Vaccines*, Academic Press. San Diego pp. 59-72 (1996).

Hammer et al., "Spontaneous Inflammatory Disease in Transgenic Rats Expressing HLA-B27 and Human $\beta_2$m: An Animal Model of HLA-B27-Associated Human Disorders" *Cell* 63;1099-1112 (Nov. 30, 1990).

Kühu et al., "Interleukin-10-Deficient Mice Develop Chronic Enterocolitis" *Cell* 75:263-274 (Oct. 22, 1993)3

Lebens et al., "Large-Scale Production of *Vibrio cholerae* Toxin B Subunit for Use in Oral Vaccines" *Bio/Technology* 11:1574-1578 (Dec. 11, 1993).

Lycke, "The Mechanism of cholera toxin adjuvanticity" *Res. Immunol.* 148:504-520 (Dec. 31, 1997).

McSorley etal., "Selective tolerizatiom of TH1-Like cells after nasal administration of a cholera toxid-LACK conjugate" *Eur. J. Immunol.* 28:424-432 (1998).

Mekalanos et al., "Cholera toxin genes: nucleotide sequence, deletion analysis and vaccine development" *Nature* 306:551-557 (Dec. 8, 1983).

Mombaerts et al., "Spontaneous Development of Inflammatory Bowel Disease in T Cell Reeptor Mutant Mice" *Cell* 75:275-282 (Oct. 22, 1993).

Neurath et al., "Antibodies to Interleukin 12 Abrogate Established Experimental Colitis On Mice" *J. Exp. Med.* 182:1281-1290 (Nov. 1995).

Podolsky, "Inflammatory Bowel Disease" *New Engl. J. Med.* 325:928-937 (Sep. 26, 1991).

Powrie et al., "Inhibition of Th1Responses Prevents Inflammatory Bowel Disease in *scid* Mice reconstituted with $CD45RB^{hi}$ CD4' T Cells" *Immunity* 1:553-562 (Oct. 1994).

Sadlack et al., "Ulcerative Colitis-Like Disease in Mice with a Disrupted Interleukin-2 Gene" *Cell* 75:253-261 (Oct. 22, 1993).

Snider, "The Mucosal Adjuvant Activities of ADP-Ribosylating Bacterial Enterotoxins" *Crit Rev. Immunol.* 15(3&4) : 317-348

Strober et al., "Reciprocal IFN-$\gamma$ and TGF-$\beta$ responses Regulate the occurence of mucosal inflammation" *Immunol. Today* 18(2) : 61-64 (Feb. 1, 1997).

Strober and Ehrhardt, "Chronic Intestinal Inflammation: An Unexpected Outcome on Cytokine or T cell Receptor Mutant Mice" *Cell* 75:203-205 (Oct. 22, 1993).

Strober and Neurath, "Immunological diseases of the gastrointestinal tract" *Clinical Immunology-Principles and Practice* (R.R. Rich, ed) Mosby, St. Louis, Chapter 94 pp. 1401-1428 (1995).

Sun et al. "Cholera toxin B subunit: An efficient transmucosal carrier-delivery system for induction of peripheral immunological tolerance" *Proc. Natl. Acad. Sci. USA* 91:10795-10799 (Nov. 1994).

Van der Heijden and Stok, "Improved procedure for the isolation of functionally active lymphoid cells from the murine intestine" *J. Immunol. Meth.* 103:161-167 (1987).

Woogen et al., "Inhibition of Murine T Cell Activation by Cholera Toxin B Subunit is not Mediated through the Phosphatidylinositol Second Messenger System" *J. Immunol.* 150:3274-3283 (Apr. 15, 1993).

Woogen et al., "Inhibition of murine lymphocyte proliferation by the B subunit of cholera toxin" *J. Immunol.* 139: 3764-3770 (Dec. 1, 1987).

Yankelevich et al., "Prevention of Acute Graft-Versus-Host Disease by Treatment with a Novel Immunosuppressant: Cholera Toxin B Subunit" *J. Immunol.* 154(7):3611-3617 (1995).

Yankelevich et al., "Differential Induction of Programmed Cell Death in CD and $CD4^+$T Cells by the B Subunit of Cholera Toxin" *Cell. Immunil.* 168:229-234 (1996).

* cited by examiner

METHODS OF TREATING INFLAMMATORY BOWEL DISEASE USING CHOLERA TOXIN B SUBUNIT

The present application is a 35 U.S.C. § 371 national phase application from, and claims priority to, international application PCT/US00/30837, filed Nov. 9, 2000 (published under PCT Article 21(2) in English), which claims priority to U.S. provisional patent application Ser. No. 60/165,111, filed Nov. 12, 1999, which applications are incorporated herein in their entirety by reference.

BACKGROUND OF THE INVENTION

1. Field of the Invention

The present invention relates to a method of treating or preventing an inflammatory bowel disease in a subject by administering cholera toxin B subunit (CT-B) to the subject. Further provided are methods for treating or preventing inflammation and/or an autoimmune disorder in a subject and for decreasing interferon gamma (IFN-γ) and/or interleukin 12 (IL-12) activity in a subject by administering CT-B to the subject.

2. Background Art

Inflammatory bowel disease (IBD), encompassing Crohn's disease (CD) and ulcerative colitis (UC), is an idiopathic chronic disease occurring with increasing frequency in Western populations (1, 2). Various animal models of chronic intestinal inflammation have been established which have provided new insights into the pathogenesis of IBD (3). These include mice carrying transgenes of HLA-B27 and β2-microglobulin (4) and mice in which the genes for interleukin-2 (IL-2) (5), interleukin-10 (IL-10) (6) and the alpha or beta chain of the T cell receptor (7) have been inactivated by homologous recombination. In addition, a colitis model has been recently established by the adoptive transfer of normal CD45RBhi T cells from BALB/c mice to C.B.-17 scid mice, wherein the transferred T cells manifest a Th1 cytokine response associated with granulomatous inflammation. This experimental colitis can be prevented by systemic administration of anti-interferon-gamma (anti-IFN-γ) (two doses) and by systemic, daily administration of recombinant IL-10 (rIL-10), given at the same time disease is induced, but not with recombinant interleukin-4 (rIL-4) (8). The observation that administration of IL-10, a product of Th2 cell differentiation, but not IL-4, which is also a product of Th2 cell differentiation, can prevent experimental colitis, underscores the unpredictability of administering cytokines to prevent or treat IBD.

The intrarectal instillation of the hapten agent, 2,4,6-trinitrobenzene sulfonic acid (TNBS) in SJL mice results in a colitis that resembles many features of human Crohn's disease. In particular, histologic analysis reveals a colitis that is transmural in nature and associated with granuloma formation. In addition, studies of the genesis of the immune response to the rectal administration of TNBS have shown that lesional T cells produce significantly increased amounts of IFN-γ and reduced amounts of interleukin-4 (IL-4) and lesional antigen presenting cells (APC) produce increased amounts of IL-12. These findings indicate that the colitis occurring in these mice is due to a dysregulated Th1-mediated immune response (9).

Cholera holotoxin (CT) is composed of a monomeric "A" subunit bound to five identical "B" subunits. The A subunit (CT-A) affects G protein signaling activity by inhibiting adenylate cyclase while the B subunit (CT-B) facilitates the entry of the A subunit into the cell by binding to GM 1 ganglioside on the cell surface. The ability of the holotoxin to act as a potent immunogen and mucosal adjuvant (10–12) has largely been attributed to subunit A, but recent evidence indicates that CT-B also has immunogenic effects. In particular, it appears that CT-B can also act as a mucosal adjuvant, at least under certain circumstances (13–15). In addition, oral administration of antigen coupled to recombinant CT-B (rCT-B) potentiates the induction of oral tolerance to the coupled antigen. Because in this case, the CT-B must be coupled to the antigen to have an effect, CT-B may be acting through its capacity to focus antigen on lymph cells rather than act as an immunomodulator (16–19). However, the effect of CT-B coupled to antigen is antigen-specific and thus has no polyclonal effect on the immune function.

The present invention overcomes previous shortcomings in the treatment of autoimmune disorders such as IBD by providing methods of treating or preventing autoimmune disease such as IBD by the administration of cholera toxin subunit B to a subject in need of such treatment. The administration of cholera toxin subunit B to a subject by the methods of this invention can also treat or prevent inflammation and reduce the activity of IL-12 and IFN-γ.

SUMMARY OF THE INVENTION

The present invention provides a method of treating or preventing inflammation in a subject, comprising administering to the subject an effective amount of cholera toxin subunit B.

The present invention also provides a method of decreasing the activity of interferon gamma in a subject, comprising administering to the subject an effective amount of cholera toxin subunit B.

Further provided is a method of decreasing the activity of IL-12 in a subject, comprising administering to the subject an effective amount of cholera toxin subunit B.

Additionally, the present invention provides a method of treating or preventing a Th1 T-cell mediated autoimmune disorder in a subject, comprising administering to the subject an effective amount of cholera toxin subunit B.

The present invention may be understood more readily by reference to the following detailed description of specific embodiments and the Examples included herein.

DESCRIPTION OF THE PREFERRED EMBODIMENTS

As used herein, "a" or "an" can mean one or more. For example, "a" cell can mean one cell or more than one cell.

The present invention is based on the surprising and unexpected discovery that the administration of the B subunit of cholera toxin alone (in the absence of the A subunit), is effective in downregulating inflammatory cytokines (e.g., IFN-γ and IL-12) and therefore can be used to treat or prevent an inflammatory response associated with these cytokines. Thus, the present invention provides a method of treating or preventing inflammation in a subject, comprising administering to the subject an effective amount of cholera toxin subunit B (CT-B).

As used herein, "effective amount" means an amount of CT-B that effectively reduces inflammation in the subject, as determined by relief of symptoms of inflammation (e.g., pain, swelling, redness, fever, heat sensation, tenderness, stiffness, etc.) or by a change in the clinical and/or histological parameters well known in the art to be associated with inflammation. For example, an amount of CT-B which results in a reduction or elimination of symptoms, or which results in a change in clinical and/or histological parameters from abnormal to normal or less abnormal is an effective amount of CT-B.

More specifically, an effective amount of CT-B is that amount which reduces or reverses the histological and clinical manifestations of the inflammation to a greater degree than observed in controls, as described herein. For example, the inflammation to be treated by the methods of this invention can be caused by an inflammatory bowel disease. The ability of a given amount of CT-B of this invention to reduce the inflammatory response of an inflammatory bowel disease is determined by evaluating the histological and clinical manifestations, as set forth herein, of the subject before and after administration of the CT-B and quantitating the amount of reduction of the inflammation in response to given amounts. If, for a given amount, the reduction in inflammatory response is greater than the amount of reduction in inflammatory response in a control subject, then the amount of CT-B administered to achieve such reduction is determined to be an amount effective in reducing the inflammatory response of an inflammatory bowel disease. This analysis is also used for determining an effective amount of CT-B for treating or preventing other types of inflammation, as would be well known to the artisan.

An effective amount of CT-B for treating or preventing inflammation can also be determined by monitoring changes in the amount or in the activity of various biological substances, such as cytokines, which are associated with inflammation (e.g., IL-12 and IFN-$\gamma$), as are well known in the art and as described herein.

The present invention also provides a method of treating or preventing the inflammatory response of an inflammatory bowel disease (IBD) in a subject, comprising administering to the subject an effective amount of cholera toxin subunit B. As used herein, an "inflammatory response of an IBD" refers to a condition of the colon characterized by a state of inflammation ("colitis") in which one or more of the following histological characteristics, as are well known in the art, are detectable: leukocyte infiltration, thickening of the colon wall, transmural infiltrations, loss of goblet cells, ulcerations, granulomas and fibrosis. Clinical symptoms of an inflammatory response (colitis) of an IBD can include, but are not limited to, diarrhea, rectal prolapse, weight loss, abdominal pain, dehydration and splenomegaly.

The present invention further provides a method of decreasing the activity of interferon gamma in a subject, comprising administering to the subject an effective amount of cholera toxin subunit B (CT-B) and a method of decreasing the activity of IL-12 in a subject, comprising administering to the subject an effective amount of cholera toxin subunit B (CT-B).

As used herein, "decreasing the activity" of substances such as the cytokines of this invention means to decrease the amount of the substance produced in the cell either at the level of mRNA production or at the level of protein production and/or to decrease the amount of the substance released or secreted from the cell which produces the substance. Additionally, the activity of a substance can be decreased by modulating the ability of the substance to interact with other substances with which it is known to react to produce a specific physiological effect (e.g., blocking the binding of a ligand to its receptor).

The methods of this invention can be used, for example, to treat a subject who is at risk of developing, or is diagnosed as having, a colitis caused by inflammatory bowel disease, which can be, but is not limited to, Crohn's disease or ulcerative colitis.

Further provided in this invention is a method of treating or preventing a Th1 T-cell mediated autoimmune disorder in a subject, comprising administering to the subject an effective amount of CT-B. As used herein, an effective amount of CT-B is an amount of CT-B which reduces or eliminates the symptoms associated with the autoimmune disorder, as compared to a control or results in a change in clinical parameters from abnormal to normal or less abnormal, as would be well known in the art for autoimmune disorders.

The autoimmune disorder which can be treated or prevented by the methods of this invention can be, but is not limited to, inflammatory bowel disease, multiple sclerosis, rheumatoid arthritis, pernicious anemia, autoimmune gastritis, psoriasis, Bechet's disease, idiopathic thrombocytopenic purpura, Wegener's granulomatosis, autoimmune uveitis, autoimmune thyroiditis, autoimmune oophoritis, bullous pemphigoid, pemphigus, polyendocrinopathies, Still's disease, Lambert-Eaton myasthenia syndrome, myasthenia gravis, Goodposture's syndrome, autoimmune orchitis, systemic lupus erythematosus, Sjogren's syndrome and ankylosing spondylitis, as well as any other autoimmune disorder now known or later identified.

The subject of this invention can be any animal which is susceptible to inflammation and/or autoimmune disease and/or produces IL-12 and/or IFN$\gamma$ and can be treated by the methods of this invention. However, mammals, and in particular, humans, are the primary therapeutic target.

The CT-B of this invention can be purchased either as purified CT-B or recombinant CT-B (rCT-B) through commercial sources (e.g., List Biological Laboratories) or can be produced by methods standard in the art of molecular biology for the production of recombinant proteins and purification of proteins.

In the present invention, the CT-B can be administered to a subject in a pharmaceutically acceptable carrier. By "pharmaceutically acceptable" is meant a carrier that is not biologically or otherwise undesirable, i.e., the carrier may be administered to a subject, along with the CT-B, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The CT-B may be administered orally, parenterally (e.g., intravenously), by intramuscular injection, by intraperitoneal injection, transdermally, extracorporeally, intrarectally, topically or the like, although oral administration is typically preferred. The exact amount of the CT-B required will vary from subject to subject, depending on the species, age, weight and general condition of the subject, the severity of the disease or condition being treated, the particular CT-B used, its mode of administration and the like. Thus, it is not possible to specify an exact amount of CT-B to administer. However, an appropriate amount can be determined by one of ordinary skill in the art using only routine experimentation given the teachings herein (see, e.g., Remington's Pharmaceutical Sciences; ref 22).

Parenteral administration of the CT-B of the present invention, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

Suitable carriers for use in the present invention include, but are not limited to, pyrogen-free saline and sodium bicarbonate. For parenteral administration, a sterile solution or suspension is prepared in saline that may contain additives, such as ethyl oleate or isopropyl myristate, and can be injected, for example, into subcutaneous or intramuscular tissues.

Suitable carriers for oral administration of CT-B include one or more substances which may also act as flavoring agents, lubricants, suspending agents, or as protectants. Suitable solid carriers include calcium phosphate, calcium carbonate, magnesium stearate, sugars, starch, gelatin, cellulose, carboxypolymethylene, or cyclodextrans. Suitable liquid carriers may be water, pharmaceutically accepted oils, or a mixture of both. The liquid can also contain other suitable pharmaceutical additions such as buffers, preservatives, flavoring agents, viscosity or osmo-regulators, stabilizers or suspending agents. Examples of suitable liquid carriers include water with or without various additives, including carboxypolymethylene as a pH-regulated gel.

Alternatively, the CT-B may be microencapsulated with either a natural or a synthetic polymer into microparticles 4–8 μm in diameter, which target intestinal lymphoid tissues and produce a sustained release of antibody for up to four weeks.

For treatment of humans, CT-B would typically be orally administered in a daily dosage of between at least about 0.05 mg/kg body weight and at least about 0.5 mg/kg body weight, although a more preferred range is between at least about 0.05 mg/kg body weight and at least about 0.075 mg/kg body weight, until symptoms subside or clinical parameters indicate improvement. However, the age, weight and condition of the individual must be considered in determining a final dose. One skilled in the art will realize that dosages are best optimized by the practicing physician and methods for determining dosages are described for example, in *Remington's Pharmaceutical Sciences* (22).

As an example, to evaluate the efficacy of CT-B treatment in human subjects diagnosed with IBD, the following studies are performed. Patients with active inflammation of the colon and/or the terminal ileum who have failed standard prednisone therapy (parenterally or orally) for control of the IBD are selected for treatment of acute disease. CT-B can also be administered as maintenance therapy, for example, in patients who have achieved remission by standard steroid therapy or by treatment with anti-TNF-α antibodies or who are on post-surgical immunosuppressive medication.

Drug efficacy is monitored via colonoscopy. Patients are randomized to two different protocols. In one protocol, subjects remain on initial steroid dosage and in the second protocol, subjects have their steroid dosage tapered after receiving CT-B therapy.

Treatment can consist of a single daily oral dosage of 0.05 mg/kg to 0.075 mg/kg body weight of CT-B until symptoms of the colitis subside or clinical parameters indicate improvement of the subject's condition. The blood pressure, pulse and temperature of the subject are monitored. Subjects are given a laboratory evaluation consisting of a complete blood count (CBC) with differential, platelet count, SMA-18 chemistry profile, erythrocyte sedimentation rate (ESR) and a C-reactive protein assay at 1) the time of CT-B administration, 2) 24 hours later, 3) 72 hours later, 4) two weeks later, 5) four weeks later, 6) six weeks later, and 7) eight weeks after administration.

Subjects can also undergo routine colonoscopy with video surveillance at the time of the administration of CT-B and again at two, four, six and eight weeks after initiation of therapy.

Additionally, serum samples from the subjects are assayed by ELISA or similar assays for IL-12 and/or IFN-γ levels to monitor drug efficacy. Also, tissue biopsy samples obtained during colonoscopy are cultured and assayed for IL-12 and/or IFN-γ levels. The measurement of these cytokines is routine in the art and can be carried out with kits which are commercially available or with standard laboratory reagents.

The efficacy of administration of a particular dose of CT-B in treating an autoimmune disease in a subject diagnosed as having an autoimmune disease are determined by standard methods of evaluation of the particular signs, symptoms and objective laboratory tests for a particular autoimmune disease, as would be well known in the art. For example, if 1) a subject's frequency or severity of recurrences is shown to be improved; 2) the progression of the disease is shown to be stabilized; or 3) the need for use of other immunosuppressive medications is lessened, based on a comparison with an appropriate control group and knowledge of the normal progression of disease in the general population or the particular individual, then a particular treatment is considered efficacious.

The efficacy of CT-B in preventing inflammation or an autoimmune disease in a subject not known to presently have inflammation or an autoimmune disease but known to be at risk of developing inflammation or an autoimmune disease is determined by evaluating standard signs, symptoms and objective laboratory tests, as would be known to one of skill in the art, over time. This time interval may be large, with respect to the development of an autoimmune disease (years/decades) or very short (hours/days) with respect to inflammation. The determination of who would be at risk for the development of inflammation or an autoimmune disease would be made based on a recent history of the patient with respect to exposure to or involvement with factors known to induce inflammation or an autoimmune disease, as well as a current knowledge of the known risk factors for a particular autoimmune disease familiar to a clinician in this field, such as a particularly strong family history of autoimmune disease.

The present invention also provides a method of inducing apoptosis in a population of T cells in a subject comprising administering to the subject an effective amount of cholera toxin subunit B.

As used herein "apoptosis" refers to programmed cell death that has distinctive morphological and structural features that are different from those of pathological cell death or necrosis. The apoptotic process is characterized by nuclear fragmentation and cytoplasmic budding that lead to the formation of apoptotic bodies.

In the present invention, the T cells that undergo apoptosis are prime activated T ells also referred to as T cells that are activated by antigen to undergo apoptosis or as activated memory effector T cells.

The present invention is more particularly described in the following examples which are intended as illustrative only since numerous modifications and variations therein will be apparent to those skilled in the art.

EXAMPLE I

The basic plan of these studies was to induce colitis in mice by intra-rectal administration of TNBS and then determine the effect of treatment with rCT-B. Accordingly, TNBS (3.75 mg) in 50% ethanol was administered intrarectally to 5 week old SJL/J mice to induce acute disease. For induction of chronic disease, 2.5 mg of TNBS in 40% ethanol was administered to mice. Concomitantly, some of the mice were given an oral preparation containing either 100 µg recombinant CT-B (rCT-B) in 500 µl of $NaHCO_3$ daily for 4 days and other mice were given $NaHCO_3$ alone.

Oral administration of rCT-B was shown to reproducibly lead to a significant decrease in disease morbidity, as characterized by rapid recovery of weight loss, and a decrease in mortality, as compared to untreated TNBS-colitis mice. Furthermore, the colons of mice treated with rCT-B 5 days after the induction of the colitis, showed no macroscopic signs of colitis. While microscopic histologic analysis of the colons of untreated mice with TNBS-induced colitis revealed the presence of a transmural inflammation characterized by dense lymphocytic infiltrates, loss of goblet cells, reduction of mucin and epithelial ulcerations, the colons of treated mice either had no evidence of inflammation or had signs of resolving colitis and reconstitution of epithelial cells, reappearance of goblet cells and reduction of lymphocytic infiltration.

These features were specific for rCT-B and not due to preparation contaminants, because in separate experiments, oral administration of purified culture products of a variant of Vibrio cholerae $A^-B^-$, which is devoid of the DNA encoding CT-A and CT-B (20), did not ameliorate colitis. In addition, the endotoxin content of the active and inactive preparations, as determined by quantitative chromogenic LAL test (QCL-1000, Bio Whittaker, Walkersville, Md.), was approximately the same (0.4 and 0.3 EU/single dose, respectively).

Upon evaluation of cytokine production of lamina propria mononuclear cells isolated from the colons of mice from the different groups, a significant increase in IFN-γ production was observed in untreated mice with TNBS-induced colitis, as previously described (9). In contrast, mice with TNBS-induced colitis that were treated with rCT-B exhibited a level of IFN-γ secretion which was not different from that of control mice (50% ethanol-treated mice and 50% ethanol-treated mice and rCT-B). This reduction in IFN-γ production was not associated with an increased IL-4 production, as values observed in the TNBS-colitis mice treated with rCT-B were not different from those observed in the untreated TNBS-induced colitis mice which did not receive rCT-B In addition, no difference in the production of TGF-β and IL-10 was observed between the rCT-B-treated mice and control mice. Thus, rCT-B was able to prevent the induction of TNBS-colitis without influencing the production of regulatory cytokines such as IL-10 and TGF-β.

Because increased IFN-γ production in TNBS-colitis is driven by IL-12 production (9), the effect of rCT-B on IL-12 production was also investigated. IL-12 production was detected in cultures of lamina propria cells (LPMC) obtained from mice with TNBS-colitis, but not in cultures of LPMC isolated from mice with TNBS-induced colitis treated with rCT-B. Taken together, these data indicate that rCT-B treatment prevents the induction of TNBS-induced colitis through the suppression of IL-12 and the downregulation of IFN-γ secretion.

On the basis of previous observations that the treatment of TNBS-induced colitis with anti-IL-12 monoclonal antibodies results in apoptosis of activated Th1 T cells (21), lamina propria tissue sections from colons of mice with TNBS-colitis treated rCT-B and from untreated TNBS-induced colitis mice were evaluated for the presence of apoptotic lymphocytes. Tissue sections from rCT-B treated mice demonstrated an increased number of apoptotic lymphocytes when compared to untreated TNBS-induced colitis mice. These results demonstrate that IL-12 is a necessary cytokine for the viability of the Th1 T cell and in states in which IL-12 secretion is decreased, the Th1 T cell necessary for the ongoing inflammation undergoes apoptosis.

The immunological profiles of the mice treated with TNBS to induce acute disease and the mice treated with TNBS to induce chronic disease were the same. Administration of rCT-B to TNBS-treated mice with chronic disease from day 5 to day 9 following the induction of colitis led to a reversal of the inflammation and a reduction in both IFN-γ and IL-12.

In summary, these data demonstrate that rCT-B alone (i.e., in the absence of CT-A and/or without coupling to antigen) has direct immunomodulating effects through the suppression of IFN-γ and IL-12 secretion. This effect of rCT-B occurs in the absence of linkage to an antigen and the suppression is not related to the induction of tolerogenic suppressor cells producing TGF-β, IL-10 or IL-4. These data also show that treatment of mice with rCT-B can effectively prevent the induction of TNBS-colitis, a Th1 mediated inflammation. In that Crohn's disease demonstrates a similar immunologic profile, these studies indicate that oral administration of CT-B can be used in the treatment of inflammatory bowel disease, as well as in the treatment of other autoimmune states.

EXAMPLE II

Production and purification of rCT-B.

The Vibrio Cholerae strain 0395-tacCTB, lacking the CT-A gene, was used as a source to produce rCT-B and Vibrio Cholerae, lacking the CT-A and CT-B gene (20), was used as a source for control material to identify culture contaminants. rCTB was produced and purified according to the protocol described by Lebens et al. (23) with minor modifications. In brief, rCT-B was extracted from the medium of Vibrio Cholerae cultures by precipitation with sodium hexametaphosphate. The precipitate was spun down and redissolved in a minimal volume of 100 mM sodium phosphate buffer, pH 8 and dialyzed extensively against 10 mM sodium phosphate buffer, pH 7. The dialysate was then centrifuged at 15000 g for 20 min. to remove undissolved material. As a final purification step, the material was subjected to ion exchange chromatography through a CM-Sepharose column (CL-6B Pharmacia, Biotech AB, Upsala, Sweden) and vacuum dialyzed using a colloid ion membrane (cut off $10^5$ MW). CT-B concentration was determined by solid-phase ELISA using immobilized $G_{M1}$ ganglioside (Sigma Chemical Co, Milan, Italy) as a primary capture system and goat anti-cholera toxin B subunit antibody (Calbiochem, La Jolla, Calif.) and peroxidase-labeled anti-goat antibody (KPL, Gaithersburg, Md.) as secondary antibody detection system. rCT-B concentrations were obtained with reference to a standard curve obtained using known amount of purified cholera toxin B subunit (Sigma).

The amount of endotoxin present in the final preparations was determined by Quantitative Chromogenic Limulus Amebocyte Lysate test (QLC-1000, Biowhittaker, Walkersville, Md.) according to the manufacturer's instructions.

Induction of Colitis.

Specific pathogen-free 4–5 week old male SJL/J mice were obtained from Charles River (Calco, Italy) and the National Cancer Institute (NCI, Bethesda, Md.) and maintained in a pathogen-free environment animal facility at the Istituto Superiore di Sanita' and the pathogen-free animal facility at the National Institute of Allergy and Infectious Diseases (NIAID, National Institutes of Health). To insure a pathogen-free state, mice were tested and shown to be free from >20 known bacterial and viral murine pathogens. Experiments were performed 3 days after the arrival of the animals. Animals were treated in accordance with the European Community and National Institutes of Health guidelines and the Institute Ethical Committee. To induce TNBS-colitis for studies of regulation of colitis induction, 3.75 mg of TNBS (pH 1.5–2.0; Sigma Chemical Co. St. Louis, Mo.) in a 50% ethanol was administered per rectum to lightly anesthetized mice through a 3.5 F catheter inserted into the rectum. Alternatively, to induce colitis for studies of established inflammation, 2.5 mg of TNBS in 45% ethanol was administered per rectum. The catheter tip was inserted 4 cm proximal to the anal verge, 150 µl of fluid (TNBS/ethanol or 50% ethanol alone) was slowly instilled into the colon, and the mouse was held in a vertical position for 30 seconds.

In some experiments, 6 mg of the haptenizing agent, oxazolone (4-ethoxymethylene-2-phenyl-2-oxazolin-5-one) (Sigma Chemical Co) in 150 µl of a 1:1 $H_2O$/ethanol mixture (24) was administered intrarectally according to the method described above.

Feeding of rCT-B.

Mice were fed with 100 µg or 10 µg of RCT-B in 500 µl of 0.35M $NaHCO_3$ or 500 µl of 0.35M $NaHCO_3$ every day, over a 4 day period, using a 18 gauge feeding needle. Animals were randomized at the start of feedings to receive either TNBS/ethanol or 50% ethanol per rectum. Mice treated with 50% ethanol intrarectally and who had received 500 µl of 0.35M $NaHCO_3$ alone were used as controls for TNBS-colitis mice, while mice treated with 50% ethanol intrarectally and oral rCT-B administration were used as control for the effect of rCT-B oral administration.

Histologic Assessment of Colitis.

Tissues removed from mice at indicated times of death were fixed in 10% neutral buffered formalin solution (Sigma Chemical Co) and then embedded in paraffin, cut into tissue sections and stained with hematoxylin and eosin. Stained sections were examined for evidence of colitis using the following criteria: the presence of lymphocyte infiltration, elongation and/or distortion of crypts, frank ulceration, and thickening of the bowel wall. The degree of inflammation on microscopic cross-sections of the colon was graded semiquantitatively from 0 to 4 (0: no evidence of inflammation; 1: low level of lymphocyte infiltration with infiltration seen in less<10% hpf, no structural changes observed; 2: moderate lymphocyte infiltration with infiltration seen in 10–25% hpf, crypt elongation, bowel wall thickening which does not extend beyond mucosal layer, no evidence of ulceration; 3:_high level of lymphocyte infiltration with infiltration seen in 25–50% hpf, high vascular density, thickening of bowel wall which extends beyond mucosal layer; 4: marked degree of lymphocyte infiltration with infiltration seen in >50% hpf, high vascular density, crypt_elongation with distortion, transmural bowel wall thickening with ulceration).

Isolation of Lamina Propria Mononuclear Cells (LPMC).

LPMC were isolated from freshly obtained colonic specimens using a modification of the technique described by Van der Heijden and Stok (25). The colonic specimens were initially washed in HBSS-calcium magnesium free (Hyclone, Europe Ltd., Cramlington, England), cut into 0.5-cm pieces and incubated in HBSS containing EDTA 0.75 mmol/L and dithiothreitol 1 mmol/L (Sigma Chemical Co) at 37° C. for 15 minutes for 2 cycles. The tissue was then digested further in RPMI 1640 (Hyclone) containing collagenase D 400 U/ml and DNase 10.01 mg/ml (Boehringer Mannheim Biochemicals, Indianapolis, Ind.) in a shaking incubator at 37° C. The LPMC released from the tissue were then resuspended in 100% Percoll, layered under a 40% Percoll gradient (Pharmacia Biotech AB), and then subjected to centrifugation to obtain the lymphocyte-enriched population at the 40–100% Percoll interface.

Culture of LPMC.

Cultures of LPMC for evaluation of IFN-γ, IL-12, and IL-10 secretion were maintained in complete medium consisting of RPMI 1640 supplemented with 2 mM L-glutamine, 10 mM Hepes buffer, 10 µg/ml gentamycin, 100 U/ml each of penicillin and streptomycin and 10% fetal calf serum (FCS) (Hyclone). Cultures of LPMC for evaluation of TGF-β production, were maintained in serum-free media supplemented with 1% nutridoma-SP (Boehringer Mannheim Biochemicals).

Stimulation and Measurement of Cytokine Production by LPMC.

To measure the capacity of isolated LPMC to produce cytokines, the LPMC populations were cultured in complete medium (or serum-free media in the case of TGF-β) at ($10^6$ cells/ml in 24-well plates (Falcon, Becton Dickinson, Lincoln Park, N.J.) coated or uncoated with anti-CD3ε antibody (clone 145–2C11; PharMingen, San Diego, Calif.). Coating was accomplished by pre-exposure of individual wells to 10 µg/ml of murine-anti-CD3 E antibody in carbonate buffer (pH 9.6) overnight at 4° C. Culture fluid for cell populations in coated wells also contained 1 µg/ml soluble CD28 antibody (clone 37.51; PharMingen). After 48 hours of culture under these conditions (or 72 hrs for TGF-β), culture supernatants were removed and assayed for the presence of cytokines (IFN-γ, IL-10, IL-4 and TGF-β) by ELISA. To measure IL-12 production, LPMC cells were preincubated for 18 h with 1000 U/ml of recombinant murine IFN-γ (Genzyme-R&D Systems—Ltd, Abingdon, Oxon, UK) followed by stimulation with 0.03% *Staphylococcus aureus*, Cowan's strain I (SAC) (Calbiochem. La Jolla, Calif.). Culture supernatants were harvested after an additional 24 hours.

ELISA Assays.

Cytokine concentrations (except for TGF-β) were determined by commercially available specific ELISA assays using duo-paired murine cytokines as per the manufacturer's recommendations (Endogen Corp., Woburn, Mass., distributed by Tema ricerca, Italy). TGF-β concentrations were determined using the commercially available TGF-β Quantikine kit (R&D Systems). Optical densities were measured on a Bio-rad Novapath ELISA reader at a wavelength of 450 nm.

Immunohistochemistry

Colon tissue sections were frozen in embedding medium (OCT compound; Sakura Finetek, Torrance, Calif.) and cut into 5 µm thick sections. The latter were then air dried, fixed in acetone, and rehydrated in Tris-buffered saline (TBS) containing 0.05% Tween 20. Prior to staining, endogenous peroxidase was blocked with 0.3% $H_2O_2$ for 10 min and then protein blocked with 3% Rad Free (Schleicher and Schuell)

for 20 min. In the staining, sections were incubated for 30 min with anti-IL-12p40 (C17.15 1 µg or an isotype-matched control (IgG2 a) immunoglobulin), and then incubated with biotin-conjugated mouse F(ab)$_2$ anti-rat IgG (Jackson-Immunoresearch Laboratories, Bar Harbor, Me.) for 1 hour.

Subsequently, the sections were incubated with horseradish peroxidase (HRP)-streptavidin (Dupont, Boston, Mass.) for 30 min. In a final step, the sections were incubated with a metal-enhanced diaminobenzidine (DAB) substrate (Pierce, Rockford, Ill.) to reveal brown/black staining at the site of HRP localization. After staining, sections were washed in distilled water, dried and mounted in Permount (Fisher Scientific Co., Fairlawn, N.J.). Stained sections were photographed on an Axiophot microscope (Carl Zeiss Inc., Thornwood, N.Y.).

Confocal Immunofluorescence Apoptosis Studies

For detection of apoptotic cells, colon tissue sections were placed in freezing medium (OCT compound; Sakura Finetek) and frozen on dry ice. The tissue was then cut into 5 µm serial cryosections on siliconized slides and then placed initially into PBS containing 0.1% bovine serum albumin (Sigma) and then into PBS containing 2% $H_2O_2$ for 5 min to quench endogenous peroxidase activity. Tissue fixation was completed with exposure of slides for 10 min to acetone at −20° C. For tissue section analysis of TUNEL positive cells, cell permeabilization was performed by incubation with 0.1% TritonX-100, 0.1% sodium citrate solution for 2 min on ice. The labeling of degraded DNA specific to apoptotic cells were performed using an in situ fluorescein detection assay according to manufacturer's instructions (Boehringer Mannheim, Indianapolis, Ind.). In brief, after permeabilization, tissue sections were incubated in a humidified chamber with fluorescein TUNEL reaction mixture for 1 hour at 37° C. Sections were then rinsed with PBS and mounted with Vectashield (Vector Laboratories, Burlingame, Calif.). Sections were analyzed by single immunofluoresence using a Leica TCS-NT/SP confocal microscope at 40× objective, and a numerical aperture of 1.2. Fluorochromes were excited using an argon laser at 488 nm for FITC. Images were processed using the Leica TCS-NT/SP software v1.6.551.

Effect of rCT-B administration on the Course of TNBS-colitis

In initial studies, the effect of oral administration of recombinant cholera toxin subunit B (rCT-B) on the prevention of TNBS-colitis was determined. Accordingly, rCT-B (100 µg in 500 µl 0.35M NaHCO$_3$) was administered on the day of induction of TNBS-colitis and once each day thereafter for 3 days. It was found that such administration led to a reproducible inhibition of colitis induction. In particular, rCT-B-treated mice displayed a less sustained weight loss than untreated mice (i.e., mice exposed to intrarectal TNBS with NaHCO$_3$ given orally). In addition, treated mice suffered a lower mortality rate than untreated mice (at day 7: 30% in 100 µg rCT-B treated mice as compared to 83% in untreated TNBS-colitis mice). Control mice (given 50% ethanol alone) administered rCT-B by mouth in the absence of TNBS administration per rectum exhibited a weight loss pattern and maintained an appearance identical to control mice given 50% ethanol per rectum and NaHCO$_3$ orally; thus, rCT-B administration itself is not grossly toxic.

These effects of rCT-B on the weight of mice given TNBS per rectum were reflected in both the macroscopic and microscopic appearance of mouse colons. Thus, 4–5 days after initiation of colitis, 68% of the colons of rCT-B-treated mice showed no macroscopic evidence of colitis, whereas untreated mice all exhibited colitis. Low power microscopic analysis of untreated mice revealed the presence of severe inflammation characterized by a transmural lymphocytic colitis, loss of epithelial cells, and occasional sites of frank epithelial ulceration.

Such analysis of treated mice revealed minimal inflammation characterized by only mild lymphocyte infiltration and an intact epithelium cell layer, and this histologic display did not differ markedly from that ethanol-treated control mice. This assessment of low power microscopic changes was corroborated by semiquantitative grading of the microscopic changes as described above in which mice were assigned scores ranging from 0–4, with 4 indicating the most severe inflammation possible. Colons from mice that had received TNBS intra-rectally and NaHCO3 per os had marked inflammation and a score of 3.7±0.4 whereas colons from mice that had received TNBS intra-rectally and rCT-B/NaHCO3 per os had little or no inflammation and a score of 0.75±0.8.

In subsequent studies, the effect of rCT-B on previously established TNBS-colitis was determined. In these studies, rCT-B was adminstered using a similar regimen as described above, but in this study the administration was begun on day 5 after induction of TNBS-colitis when, as indicated above, the mice manifested severe colitis.

The rCT-B-treated mice exhibited a prompt weight gain (and were approaching a pre-colitis weight at the time of sacrifice), whereas untreated mice exhibited no weight gain. In addition, histologic analysis of mice with untreated TNBS-colitis revealed a severe transmural colitis, whereas similar mice treated with rCT-B revealed a mild, resolving colitis or normal histology. These results were corroborated by semiquantitative microscopic grading in that mice not treated with rCT-B had a score of 3.1±0.6, whereas mice treated with rCT-B had a score of 0.94±0.9.

In further studies, whether or not lower doses of orally-administered rCT-B could also exert anti-inflammatory effects on TNBS colitis was determined. Mice undergoing induction of TNBS-colitis by intra-rectal TNBS administration were treated with 10 µg (X4) of rCT-B rather than 100 µg of rCT-B, using the same four-day administration regimen described above. This low-dose rCT-B treatment also led to weight recovery in treated mice, although in this case, the recovery was somewhat delayed. In addition, mice treated with 10 µg of rCT-B manifested a lower mortality rate. It should be noted, however, that the overall (average) effect of treatment with 10 µg rCT-B was accompanied by a more variegate response pattern in that while about one third of the mice so treated exhibited an almost complete resolution of colitis, about two thirds of the mice so treated exhibited only a partial inhibition of colitis. Thus, these studies illustrate that while rCT-B still shows anti-inflammatory activity at a dose of 10 µg, this activity is distinctly less than that seen at a dose of 100 µg.

Finally, as an important control to the above studies, it was determined if the anti-inflammatory rCT-B effects were due to adventitious contaminants in the V cholerae cultures from which the rCT-B was extracted. As shown in FIG. 4, it was found that supernatants obtained from cultures of *V. cholerae* deficient in genes encoding both the cholera toxin A and B subunits prepared in an identical fashion as the rCT-B, did not have any effect on TNBS-colitis. In addition, the endotoxin content of rCT-B preparation and the supernatant preparation obtained from V cholera lacking A and B subunits as determined by the quantitative chromogenic LAL test, was approximately the same (0.4 and 0.3 EU for a single dose respectively).

Effect of rCT-B on Oxazolone-Colitis

To address the question of whether ameliorating TNBS-colitis in the present study is due to general suppression of T cell function rather than a specific effect on the T cell function involved in Th1 T cell-mediated inflammation, studies were conducted to determine if oral administration of rCT-B could prevent the induction of oxazolone-colitis, an induced colitis mediated by Th2 T cells rather than Th1 T cells and thus associated with the production of IL-4 rather than IL-12/IFN-$\gamma$ (20). Accordingly, mice were administered oxazolone per rectum with and without co-administration of 100 µg rCT-B per os and then monitored for the development of oxazolone-colitis. It was found that rCT-B administration had no effect on this form of colitis, either with respect to induced weight changes, macroscopic and microscopic changes, or to production of IL-4. In particular, lymphocytes isolated from colons of the mice with oxazolone-colitis treated with rCT-B and stimulated in vitro with anti-CD3/anti-CD28 mAbs showed the same increased production of IL-4 as observed in the untreated colitis mice (208 and 215 pg/ml, respectively), when compared to IL-4 production by lymphocytes isolated from colon of ethanol-treated control mice (12 pg/ml). In addition, the lymphocyte population from rCT-B treated and untreated mice showed the same low level of IFN-$\gamma$ following in vitro stimulation (21 and 19 U/ml, respectively). Finally, no difference was observed in the course of the colitis in the mice treated and untreated with r-CT-B as assessed by weight changes. Thus, it appears that oral rCT-B administration under the conditions tested has a selective effect on TNBS-colitis and does not appear to be acting via a general suppression of T cell proliferation.

Effect of rCT-B Administration on IFN-$\gamma$ and IL-4 Production by Mononuclear Cells Isolated from Colons of Mice with TNBS-colitis TNBS-colitis has been shown to be a Th1 T cell-mediated colitis characterized by high IFN-$\gamma$ production and low IL-4 production by lamina propria mononuclear cells (9). Production of these cytokines in mice administered rCT-B orally (rCT-B treated mice) that had undergone induction of TNBS-colitis was assessed. Accordingly, mononuclear cells from lamina propria of mice sacrificed 5 days after TNBS-administration per rectum were stimulated with anti-CD3/anti-CD28 in vitro, and then assessed for cytokine secretion by specific ELISA of culture supernatants. LPMC from mice with TNBS-colitis not treated with RCT-B displayed significantly increased IFN-$\gamma$ secretion (p=0.03), as compared to cells from control mice given ethanol alone per rectum, whereas LPMC cells from rCT-B-treated mice that had undergone induction of TNBS-colitis, displayed IFN-$\gamma$ secretion that did not differ significantly from that of cells from control mice given ethanol alone (with or without concomitant RCT-B, p>0.05). On the other hand, LPMC from rCT-B treated and control mice stimulated in the same way produced similar amounts of IL-4. Thus, it was apparent that the RCT-B treatment had resulted in the prevention of the Th1 T cell response, without at the same time inducing a Th2 T cell response. Similar studies of LPMC obtained from mice with pre-established colitis revealed a similar pattern. LPMC from mice with established colitis (obtained 9 days after colitis induction) not treated with RCT-B, displayed significantly increased IFN-$\gamma$ secretion, as compared to mice treated with rCT-B.

IFN-$\gamma$ and IL-4 production by lamina propria cells of mice treated with 10 µg RCT-B was also determined. In this case, the mice that showed complete or almost complete inhibition of colitis yielded cells that produced markedly decreased amounts of IFN-$\gamma$ and no increase in IL-4, as in mice treated with 100 µg RCT-B. In contrast, the mice that exhibited moderate or severe colitis in spite of treatment with 10 µg RCT-B produced elevated amounts of IFN-$\gamma$, albeit less than that produced by cells from untreated mice with TNBS-colitis.

Effect of CT-B treatment on TGF-$\beta$ and IL-10 Production in Mice Undergoing Induction of TNBS-colitis The ability of RCT-B to affect the Th1 T cell responses noted above could have been due to upregulation of counter-regulatory or suppressor cytokines such as TGF-$\beta$ or IL-10. To explore this possibility, TGF-$\beta$ and IL-10 production by LPMC stimulated with anti-CD3/anti-CD28 obtained 5 days after induction of TNBS-colitis was initially measured. It was found that mononuclear cells from mice with TNBS-colitis treated with RCT-B and those from mice with TNBS-colitis not treated with rCT-B manifested the same level of TGF-$\beta$ secretion and this level was not different from that of cells from control mice given ethanol alone per rectum. In addition, LPMC obtained from rCT-B-treated mice 5 days after TNBS-colitis induction when stimulated with anti-CD3/anti-CD28, produced an amount of IL-10 that was statistically the same as LPMC from mice not treated with rCT-B and, the mean IL-10 value was lower in the rCT-B treated group. This result was corroborated by the fact that measurement of IL-production by pooled LPMC from mice 9 days after TNBS-colitis and treated with rCT-B (at 5–8 days) again manifested lower IL-10 production than pooled LPMC from mice not treated with rCT-B. Thus, IL-10 production at both early and late points after colitis induction was lower in rCT-B mice than in non-treated mice, probably because IL-10 production subsides as the inflammation is resolved. It was concluded that neither upregulation of TGF-$\beta$ or IL-10 explain the anti-inflammatory effect of rCT-B administration.

Effect of CT-B on IL-12 Production in Mice Undergoing Induction of TNBS-Colitis

Another possible mechanism for the activity of rCT-B in TNBS-colitis is that it affects the production of IL-12, the APC-derived cytokine that drives the Th1 T cell response. To investigate this possibility, stimulated LPMC were obtained from mice, 5 days after TNBS-colitis induction, with *Staphylococcus aureus*, Cowan's strain I (SAC), following an 18-hour pre-incubation with IFN-$\gamma$ and then evaluated for IL-12 (p70) secretion in culture supernatants. LPMC from mice with TNBS-colitis not treated with rCT-B displayed high levels of IL-12 production, that those from rCT-B treated mice displayed almost undetectable levels of such secretion (p<0.05). In parallel studies, IL-12 production was determined in LPMC obtained from mice 9 days after TNBS-colitis induction and treated or not treated with rCT-B beginning 5 days after TNBS-colitis induction. Here again, rCT-B administration was associated with a decrease in IL-12 production. In further studies to corroborate that the administration of oral rCT-B led to a decrease in IL-12 secretion, in situ staining for IL-12 p40 was performed. A marked decrease in IL-12 p40 staining was observed in colonic tissue sections obtained from mice with TNBS-colitis treated with rCT-B at the time of TNBS-colitis induction, as compared to untreated mice. It was therefore evident that treatment of mice with rCT-B at the time of induction of TNBS-colitis or later when colitis is established profoundly down-regulates IL-12 secretion.

In further studies, IL-12 production by cells extracted from mice treated with 10 μg rCT-B was determined. In this case as well, IL-12 production paralleled the effect of rCT-B. In mice exhibiting little or no inflammation, IL-12 secretion was only slightly elevated, whereas in mice exhibiting some degree of inflammation, IL-12 secretion was considerably increased, but not to the level seen in mice with TNBS-colitis not treated with rCT-B.

Inhibition of TNBS-colitis by rCT-B is Associated with Increased Apoptosis of T Cells in the Lamina Propria Tissue sections obtained from mice 5 days after induction of TNBS-colitis were stained using the fluorescein labeled TUNEL technique to detect apoptotic cells in situ. The tissue section obtained from rCT-B treated mice displayed large numbers of randomly distributed mononuclear cells with a fluoresecent green stain indicative of apoptosis, whereas few if any such cells were noted in tissue from TNBS-colitis mice not treated with rCT-B. In further studies, apoptosis was assessed in dispersed mononuclear cells by flow cytometry. Cells which correspond predominantly in size to lymphocytes were identified in a gate by forward and side light scatter. Of this population of cells, 19% of cells from mice with rCT-B-treated TNBS-colitis were TUNEL+, whereas only 3.7% of cells from mice with untreated TNBS-colitis were TUNEL+. Thus, the cells undergoing apoptosis in rCT-B-treated mice, were at least in part, a lymphocyte population.

Although the present process has been described with reference to specific details of certain embodiments thereof, it is not intended that such details should be regarded as limitations upon the scope of the invention except as and to the extent that they are included in the accompanying claims.

Throughout this application various publications are referenced. The disclosures of all of these publications and those references cited within those publications in their entireties are hereby incorporated by reference into this application in order to more fully describe the state of the art to which this invention pertains.

REFERENCES

1. Podolsky, D. K. 1991. Inflammatory bowel disease. *New Engl. J. Med.* 325:928–937.
2. Strober, W., and M. F. Neurath. 1995. Immunological diseases of the gastrointestinal tract. in: R. R. Rich (ed) *Clinical Immunology-Principles and Practice*, Chapter 94. Mosby, St. Louis. pp. 1401–1428.
3. Strober, W., and R. O. Ehrhardt. 1993. Chronic intestinal inflammation: an unexpected outcome on cytokine or T cell receptor mutant mice. *Cell* 75:203–205.
4. Hammer, R. E., S. D. Maika, J. A. Richardson, Y. P. Tang, and J. D. Taurog. 1990. Spontaneous inflammatory disease in transgenic rats expressing HLA-B27 and human β2m: an animal model of HLAB-27-associated human disorders. *Cell* 63:1099–1112.
5. Sadlack, B., H. Merz, H. Schorle, A. Schimpl, A. C. Feller, and I. Horvak. 1993. Ulcerative colitis-like disease in mice with a disrupted interleukin-2 gene. *Cell* 75:253–261.
6. Kühn, R., J. Löhler, D. Rennick, K. Rajewsky, and W. Muller. 1993. Interleukin-10-deficient mice develop chronic enterocolitis. *Cell* 75:263–274.
7. Mombaerts, P., E. Mizoguchi, M. J. Grusby, L. H. Glimcher, A. K. Bahn, and S. Tonegawa. 1993. Spontaneous development of inflammatory bowel disease in T cell receptor mutant mice. *Cell* 75:275–282.
8. Powrie, F., M. W. Leach, S. Mauze, S. Menon, L. B. Caddle, and R. L. Coffinan. 1994. Inhibition of Th1 responses prevents inflammatory bowel disease in scid mice reconstituted with CD45RBhi CD4+ T cells. *Immunity* 1:553–562.
9. Neurath, M. F., I. Fuss, B. L. Kelsall, E. Strober, and W. Strober. 1995. Antibodies to IL-12 abrogate established experimental colitis in mice. *J. Exp. Med.* 182:1281–1290.
10. Elson, C. O. 1996. Cholera toxin as a mucosal adjuvant. In *Mucosal Vaccines*. Academic Press, San Diego. pp. 59–72.
11. Snider, D. P. 1995. The mucosal adjuvant activities of ADP-ribosylating bacterial enterotoxins. *Crit. Rev. Immunol.* 15:317–348.
12. Lycke, N. 1997. The mechanism of cholera toxin adjuvanticity. *Res. Immunol.* 148:504–520.
13. Douce, G., C. Turcotte, I. Cropley, M. Roberts, M Piazza, M. Domenghini, R. Rappuoli, and G. Dougan. 1995. Mutants of *E. Coli* heat-labile toxin lacking ADP-ribosyltransferase activity act as nontoxic, mucosal adjuvants. *Proc Natl Acad. Sci.* U.S.A. 92:1644–1648.
14. Douce, G., M. Fontana, M. Pizza, R. Rappuoli, and G. Dougan. 1997. Intranasal immunogenicity and adjuvanticity of site-directed mutant derivatives of cholera toxin. *Infect. Immun.* 65: 2821–2828.
15. DeHaan, L., R. W. Verweij, I. K. Feil, M. Holtrop, W. G. Hol, E. Agsteribbe, and J. Wilschut. 1998. Role of GM1 binding in the mucosal immunogenicity and adjuvant activity of the *E. Coli* heat-labile enterotoxin and its B subunit. *Eur. J. Immunol* 28:1243–1250.
16. Sun, J. B., J Holmgren, and C. Czerkinsky. 1994. Cholera-toxin B-subunit: an efficient transmucosal carrier-delivery system for induction of peripheral immunological tolerance. *Proc. Natl. Acad. Sci. USA.* 91:10795–10799.
17. Sun J.-B., C. Rask, T. Olsson, J. Holmgren, and C. Czerkinsky. 1996. Treatment of experimental autoimmune encephalomyelitis by feeding myelin basic protein conjugated to cholera toxin B subunit. *Proc. Natl. Acad. Sci. USA.* 93:7196–7201.
18. McSorley, S. J., C. Rask, R. Pichot, V. Julia, C. Czerkinsky, and N Glaichenhaus. 1998. Selective toleration of Th1-like cells after nasal administration of a cholera toxoid-LACK conjugate. *Eur. J. Immunol.* 28:424–432.
19. Bergerot, I., C. Ploix, J. Petersen, V. Moulin, C. Rask, N. Fabien, M. Lindblad, A. Mayer, C. Czerkinsky, J. Holmgren and C. Thivolet. 1997. A cholera toxoid-insulin conjugate as an oral vaccine against spontaneous autoimmune diabetes. *Proc. Natl. Acad. Sci.* 94:4610–4614.
20. Mekalanos, J. J., D. J. Swartz, G. D. Pearson, N. Harford, F. Groyne and M. de Wilde. 1983. Cholera toxin genes: nucleotide sequence, deletion analysis and vaccine development. *Nature.* 306:551–557.
21. Fuss, I. J., T. Marth, M. F. Neurath, G. R. Pearlstein, A. Jain, and W. Strober. 1999. Anti-IL-12 treatment regulates apoptosis of Th 1 T cells in experimental (TNBS) colitis. *Gastroenterology* 117:1078.
22. Martin, E. W. *Remington's Pharmaceutical Sciences*, Martin, latest edition, Mack Publishing Co., Easton, Pa.
23. Lebens, M., S. Johansson, J. Osek, M. Lindblad, and J. Holmgren. 1993. Large-scale production of *Vibrio Cholerae* toxin B subunit for use in oral vaccines. *Bio/Technology* 11:1574.

24. Boirivant, M., 1. J. Fuss, A. Chu, and W. Strober. 1998. Oxazolone colitis: a murine model of T helper cell type 2 colitis treatable with antibodies to interleukin 4. *J. Exp. Med.* 188:1929.
25. Van der Heijden, P. J., and W. Stok. 1987. Improved procedure for the isolation of functionally active lymphoid cells from the murine intestine. *J. Immunol. Methods.* 103:161.
26. Woogen, S. D., W. Ealding, and C. O. Elson. 1987. Inhibition of murine lymphocyte proliferation by the B subunit of cholera toxin. *J Immunology* 139:3764.
27. Woogen S. D., K. Turo, L. A. Dieleman, K. W. Beagley, and C. O. Elson. 1993. Inhibition of murine T cell activation by cholera toxin B subunit is not mediated through the phosphatidylinositol second messenger system. *J Immunol* 150:3274.
28. Elson C. O., S. P. Holland, M. T. Dertzbaugh, C. F. Cuff, A. O. Anderson. 1995. Morphologic and functional alterations of mucosal T cells by cholera toxin and its B subunit. *J Immunol.* 54:1032.

What is claimed is:

1. A method of treating inflammatory bowel disease in a subject diagnosed with inflammatory bowel disease, comprising administering to the subject a therapeutically effective amount of cholera toxin subunit B wherein cholera toxin subunit B is not administered with an antigen and wherein administration is mucosal.

2. The method of claim 1, wherein the subject is a mammal.

3. The method of claim 2, wherein the mammal is a human.

4. The method of claim 1, wherein the inflammatory bowel disease is Crohn's disease.

5. The method of claim 1, wherein the inflammatory bowel disease is ulcerative colitis.

6. The method of claim 1, wherein the administration is oral or intrarectal.

7. The method of claim 1, wherein the amount of cholera toxin subunit B administered is between at least about 0.05 mg/kg body weight and at least about 0.5 mg/kg body weight.

8. A method of decreasing the activity of interferon gamma in a subject diagnosed with inflammatory bowel disease, comprising administering to the subject a therapeutically effective amount of cholera toxin subunit B wherein cholera toxin subunit B is not administered with an antigen, and wherein administration is mucosal.

9. The method of claim 8, wherein the subject is a mammal.

10. The method of claim 9, wherein the mammal is a human.

11. The method of claim 8, wherein the inflammatory bowel disease is Crohn's disease.

12. The method of claim 8, wherein the inflammatory bowel disease is ulcerative colitis.

13. The method of claim 8, wherein the administration is oral or intrarectal.

14. The method of claim 8, wherein the amount of cholera toxin subunit B administered is between at least about 0.05 mg/kg body weight and at least about 0.5 mg/kg body weight.

15. A method of decreasing the activity of IL-12 in a subject diagnosed with inflammatory bowel disease, comprising administering to the subject a therapeutically effective amount of cholera toxin subunit B wherein cholera toxin subunit B is not administered with an antigen, and wherein administration is mucosal.

16. The method of claim 15, wherein the subject is a mammal.

17. The method of claim 16, wherein the mammal is a human.

18. The method of claim 15, wherein the inflammatory bowel disease is Crohn's disease.

19. The method of claim 15, wherein the inflammatory bowel disease is ulcerative colitis.

20. The method of claim 15, wherein the administration is oral or intrarectal.

21. The method of claim 15, wherein the amount of cholera toxin subunit B administered is between at least about 0.05 mg/kg body weight and at least about 0.5 mg/kg body weight.

* * * * *